United States Patent [19]

Black

[11] Patent Number: 5,527,778

[45] Date of Patent: *Jun. 18, 1996

[54] METHOD FOR SELECTIVE OPENING OF ABNORMAL BRAIN TISSUE CAPILLARIES

[76] Inventor: Keith L. Black, 1233 Roberto La., Los Angeles, Calif. 90077

[ * ] Notice: The term of this patent shall not extend beyond the expiration date of Pat. No. 5,434,137.

[21] Appl. No.: 389,347

[22] Filed: Feb. 16, 1995

Related U.S. Application Data

[63] Continuation-in-part of Ser. No. 59,623, May 10, 1993, Pat. No. 5,434,137.

[51] Int. Cl.$^6$ .......................... A61K 38/17; A61K 38/22; C07K 14/435
[52] U.S. Cl. .................................. 514/15; 514/17
[58] Field of Search ........................................ 514/15, 17

[56] References Cited

U.S. PATENT DOCUMENTS 5,112,596  5/1992  Malfroy-Carmine ..................... 514/17

OTHER PUBLICATIONS

Blasberg et al. "Regional Blood Flow, Capillary permeability and glucose utilization in two brain turion models: preliminary observations and pharmakinetic implications", Cancer Treatment Rep. 1981 2:3–12. Abstract.

Levin et al, "Heonistic Modeling of Drug Delivery to Malignant Brain Tumors", L. Pharmacokinetic. Biophasn 1980 83:257–96. Abstract.

Shibata et al, "(Ultrastructural) study of capillary permeability of lipsome-encapsulates cisplatin in are experimental rat Brain Tumor Model", Neurol Med Chir 1989, 29 (8):696–700. Abstract.

Watts, R. G. and Merchant, R. E. "Cerebaovascular Effects and Tumor Kinetics After a single Inbratumoral injection of human recomb, I1–2 . . . in a rat model of Glionia", Neurosurgery 1992, 31 (1) 89–98; discussion 98–99. Abstract.

Phillips et al. "Reduced Cerabral Glucose Metabolism and Increase Brain Capillary Permeability Follows High Dose Metabolism Chemotherapy: a positron emision tomographic study". Ann Neurol. 1987 21 (1) 59–63. Abstract.

Robinson P. L. et al. "Model for Drug Uptabe by Brain Tumors: Effects of Osmotic Treatment and of Diffosion in Brain". J. Cereb. Flow Metab. 1990, 10(2):153–156. Abstract.

Miyagami et al., "ACNU Delivery to maglignant cpeoia tissue by osmotic blood Brain Barrier Modification with Intracarotic Infusion q Hyperosolar Mannitol". No Shinkei Geka 1985 13(9):955–963. Abstract.

Miyagami et al. "The Effect on the Tumor Vessel Permeability by Hyperosmotic Blood Brain Barrier Disruption", No To Shinkei 1988 40(9):875–82 (Abstract).

Hodozuka et al., "Sequential Change of Capillary Permeability in the Rat Brain After Surgical Removal of a Experimental Brain Tumor", L. Neuroohcol. 1993 16(3):191–200. Abstract.

Koehler, P. J. Uses of Corticosteroids in Neuro–oncology. Anticancer Drugs 1995 61:19–33. Abstract.

Marh Jewicz et al. "Intracauotic Therapy with Etoposide and Cisplation for Malignant Brain Tumors", Cancer 1991 67:11 2844–9. Abstract.

Wiranocoska, M., "Blood Brian Barriers and Treatment of Central Nervous System Tumors, " J. Fla. Med. Assoc., 1992, 79 10:707–10. Abstract.

Yuan et al. "Vascular Permeability and Microcirulation of Gliomas and Mammary Carcinomas Transplanted in Rat and Mouse Cranial Windows". Cancer Res. 1994. 54(17) 4564–8. Abstract.

Blasberg et al., "Concurrent Measurements of Blood Flow and Transcapillary Transport in Avian Sarcoma–oiros induced experimental Brain Tumors: Implications for Chemotherapy". J. Pharmacol Exp. Ther. 1984 231 (3):724–35 Abstract.

Yamada et al., "Local Blood Flow and Capillary Permeability in the Experimental Meningeal Carcinomatosis," No To Shinkei, 1984 36(3):221–26. Abstract.

Groothius et al., "Regional Blood Flow and Blood to Tissue Transport in Five Brain Tumor Models, Implications for Chemotherapy: Prog Exp Tumor Res." 1984 27 132–53. Abstract.

Neuweh et al., "Inability of Dimethyl sulfoxide and 5–fluorouabcil to Open the Blood–Brain Barrier". Neurosurgery 1983 12(1):29–34.

Aizawa et al., "Measurement of Cerebral Blood Flow, Cerebrial Blood Volume, and Cerebral Capillary Permeability in Gluonia–Bearing Rats". Nerol. Med. Chir 1990 30 (2):113–18. Abstract.

Hiesiger et al. Opening the Blood–Brain and Blood tumor Barriers in Experimental Rat–Brain Tumors: the Effect of Intracaroted Hyper Osmolar Mannitol on Capillary Permeability and Blood Flow. Annual. Neurol. 1986 19 (1):50–9. Abstract.

Primary Examiner—Christina Y. Chan
Assistant Examiner—Phlynn Touzeau
Attorney, Agent, or Firm—Poms, Smith, Lande & Rose

[57] ABSTRACT

A method for selectively opening abnormal brain tissue capillaries of a mammal in order to allow selective passage of both low and high molecular weight neuropharmaceutical agents into abnormal brain tissue. The method utilizes direct infusion of bradykinin or bradykinin analog into the carotid artery. The dose of bradykinin or bradykinin analog is maintained at levels which provide opening of abnormal brain tissue capillaries without opening normal brain capillaries. The method is useful for introducing a wide variety of neuropharmaceutical agents selectively to brain tumors and other abnormal brain tissue.

12 Claims, 12 Drawing Sheets

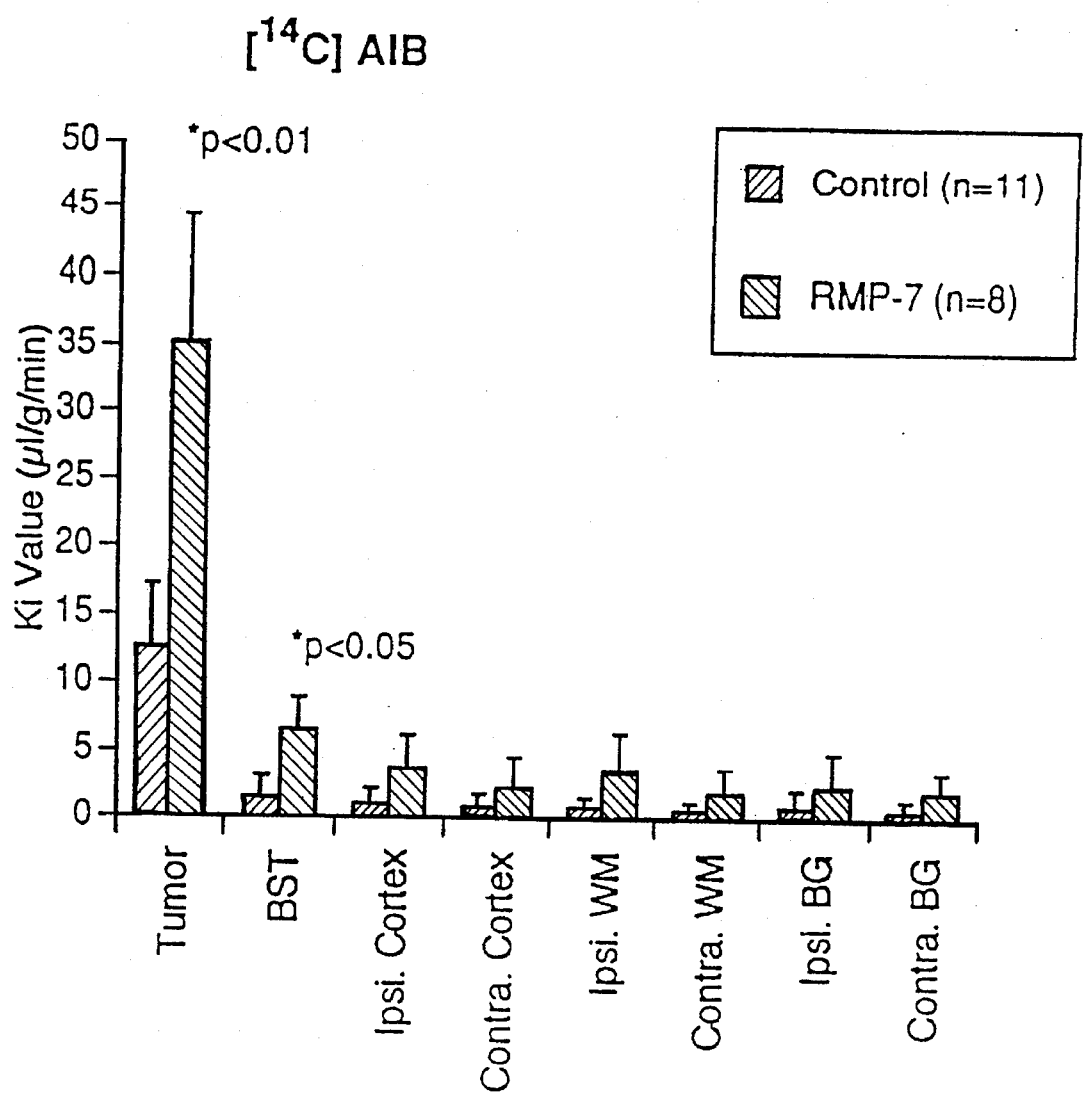

METHOD FOR SELECTIVE OPENING OF ABNORMAL BRAIN TISSUE CAPILLARIES

BACKGROUND OF THE INVENTION

This application is a continuation-in-part of application Ser. No. 08/059,623, filed on May 10, 1993, U.S. Pat. No. 5,434,137.

1. Field of the Invention

The present invention relates generally to methods for increasing the permeability of the blood-brain barrier in order to introduce neuropharmaceutical agents into the brain. More particularly, the present invention is directed to a method which selectively increases permeability of the blood-brain barrier in abnormal brain tissue.

2. Description Of Related Art

The publications and other reference materials referred to herein to describe the background of the invention and to provide additional detail regarding its practice are hereby incorporated by reference. For convenience, the reference materials are numerically referenced and grouped in the appended bibliography.

Capillaries within the brain include a barrier which prevents the delivery of many pharmaceutical agents to the brain. This blood-brain barrier (BBB) is present in both normal and abnormal brain tissue. The treatment of brain tissue abnormalities, such as tumors, require that the neuropharmaceutical agent be preferentially directed to the abnormal tissue. Accordingly, there has been a great deal of interest in developing techniques which are capable of opening the blood-brain barrier to allow transport of neuropharmaceutical agents to the brain (1, 2, 3, 4 and 5). None of these methods, however, are capable of selectively opening the blood-brain barrier only in the abnormal brain while leaving the blood-brain barrier in the normal brain intact.

In previous studies, it was demonstrated that intracarotid infusion of leukotriene $C_4$($LTC_4$) selectively increases the permeability in brain tumor capillaries without affecting the permeability in normal brain capillaries (6–9). The effect of $LTC_4$ on brain tumor capillaries is, however, limited to small molecules and it can only slightly increase the permeability of those small molecules in abnormal brain tissue. Accordingly, $LTC_4$ does not significantly increase the delivery of some water soluble drugs to brain tumors (10–13).

Bradykinin is a naturally occurring peptide formed from a plasma protein, high molecular weight kininogen by the action of kallikrein. Bradykinin is a very powerful vasodilator that increases capillary permeability. In addition, bradykinin constricts smooth muscle and stimulates pain receptors. Bradykinin may reduce cerebral blood flow (14, 15) and in high doses will induce breakdown of the normal blood-brain barrier (16). U.S. Pat. No. 5,112,596 discloses the intravenous administration of bradykinin and bradykinin agonists to provide a general increase of blood-brain barrier permeability which is not selective with respect to tumors or other abnormal brain tissue.

In view of the above, there is a continuing need to develop methods for selectively opening abnormal brain tissue capillaries in order to allow selective passage of neuropharmaceutical agents into abnormal brain tissue without increasing the permeability of the normal blood-brain barrier.

SUMMARY OF THE INVENTION

In accordance with the present invention, it was discovered that intracarotid artery infusion of low doses of bradykinin or a bradykinin analog selectively increases the permeability of abnormal brain tissue capillaries to both low and high molecular weight neuropharmaceutical agents. Infusion of bradykinin or a bradykinin analog into the carotid artery has previously been thought to be a drastic measure which, like cortical superfusion, is not to be used with powerful drugs such as bradykinin or a bradykinin analog except in extreme cases.

Contrary to prior thinking, the present invention involves a method wherein bradykinin or a bradykinin analog, at low dosages, is infused directly into the carotid artery. It was discovered that such infusion of low levels of bradykinin or a bradykinin analog selectively open abnormal brain tissue capillaries without opening normal brain capillaries. It was discovered that the abnormal brain capillaries are opened sufficiently by intracarotid infusion of bradykinin or a bradykinin analog to allow the passage of a variety of molecular weight (i.e. about 100 to about 70,000) neuropharmaceutical agents into the abnormal brain tissue.

As a feature of the present invention, neuropharmaceutical agents can be coadministered with the bradykinin or a bradykinin analog to provide selective delivery of the neuropharmaceutical agent to abnormal brain tissues such as tumors and cerebral abscesses.

The above discussed and many other features and attendant advantages will become better understood by reference to the following detailed description when taken in conjunction with the accompanying drawings.

BRIEF DESCRIPTION OF THE DRAWINGS

FIGS. 5A–E show graphic results of the quantitative determination of permeability using RMP-7 bradykinin analog. The regional Ki values were obtained from 10 minute experiments using [$^3$H] methotrexate (MW 454.5) and four other tracers, [$^{14}$C] aminoisobutyric acid (MW 103), p[$^{14}$C] sucrose (MW 342) and [$^{14}$C] inulin (MW 5,000) and [$^{14}$C] dextran (MW 70,000). Each bar indicates mean±SD. FIG. 5(A) shows the regional Ki value of [$^{14}$C] dextran. In tumors, the Ki value in the RMP-7 group was 10.3-fold higher than the control group (15.2±3.42 vs. 1.47±1.24; $p<0.001$). The Ki values of normal brain regions in both groups are low and there was no significant differences between two groups. FIG. 5(B) shows the regional Ki value of [$^{14}$C] sucrose. In tumors, the Ki value in the RMP-7 group was higher than the control group (16.5±3.83, n=8 vs. 9.28±3.12, n=6; $p<0.01$). The Ki values of normal brain regions in both groups are low and there was no significant differences between two groups. FIG. 5(C) shows the regional Ki values for methotrexate. The Ki values were significantly increased in the tumors (26.3±10.3, n=8 vs. 8.98±6.78, n=7; $p<0.05$). The Ki values of normal brain regions in both groups are low and there was no significant differences between two groups. FIG. 5(D) shows the regional Ki value of [$^{14}$C] inulin. The Ki values were significantly increased in the tumors (13.5±3.23, n=8 vs. 6.55±4.32, n=8; $p<0.01$). The Ki values in normal brain regions were not different between two groups. FIG. 5(E) shows the regional Ki value of [$^{14}$C] AIB. The Ki values were significantly increased in tumors (35.3±9.11, n=8 vs. 12.7±4.56, n=11; $p<0.01$) and brain surrounding tumor (BST; areas at 2 mm distance from the border of the tumor, 6.62±2.35 vs. 1.48±1.71, $p<0.05$), while the Ki values in normal brain regions more than 2 mm from tumors were not different between two groups. Ipsi. Cortex=ipsilateral cortex; Contra. Contex=contralateral cortex; Ipsi. WM=ipsilateral white matter; Contra. WM=contralateral white matter; Ipsi. BG=ipsilateral basal ganglia; Contra. BG=contralateral basal ganglia.

DETAILED DESCRIPTION OF THE PREFERRED EMBODIMENTS

Figure 1:
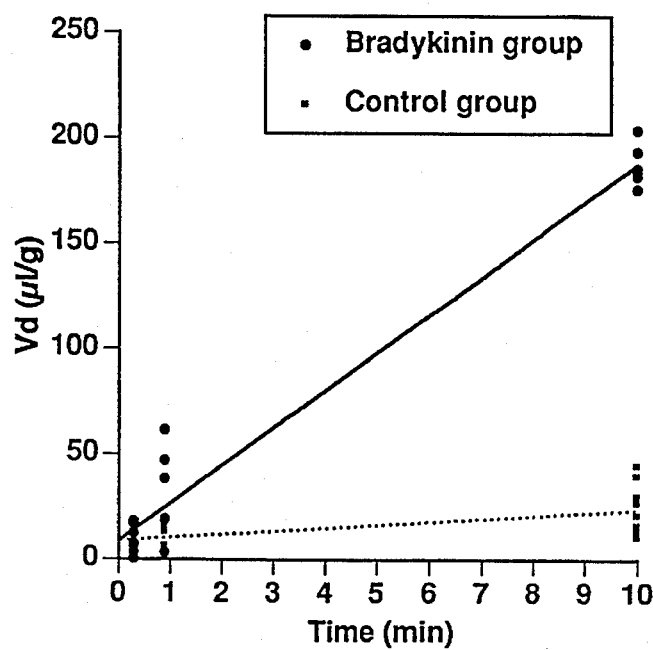
FIG. 1 is a graph showing that the selective increase in the volume of distribution in brain tumors is due to an increase in tumor permeability and not blood volume when treated with bradykinin or a bradykinin analog in accordance with the present invention.

The present invention is a method for selectively opening abnormal brain tissue capillaries of a mammal in order to allow selective passage of both low and high molecular weight neuropharmaceutical agents into the abnormal brain tissues. The present invention is applicable to treating brain tumors, abnormal tissues resulting from multiple sclerosis, ischemia and cerebral abscess. The invention is also applicable to brain tissue which is inflamed, infected or degenerated due to any number of different diseases. Examples of specific types of abnormal brain tissue include gliomas, metastatic brain tumors, head injury, meningitis, brain abscess, multiple sclerosis, subarachnoid hemorrhage.

The method involves opening the abnormal brain tissue capillaries by infusing bradykinin or a bradykinin analog into the carotid artery of the mammal. The bradykinin or bradykinin analog is infused in an amount which is sufficient to selectively open the abnormal brain tissue capillaries to allow passage of neuropharmaceutical agents, including high molecular weight agents, into the abnormal brain tissue without opening the normal brain capillaries to passage of the neuropharmaceutical agent.

Bradykinin is a naturally occurring peptide comprised of nine amino acids. The structure of bradykinin and methods for isolating and purifying bradykinin are known. Analogs of bradykinin include related peptide structures which exhibit the same properties as bradykinin but have modified amino acids or peptide extensions on either terminal end of the peptide. Examples of bradykinin analogs include [phe$^8$ (CH$_2$—NH) Arg$^9$]-bradykinin, N-acetyl [phe$^8$ (CH$_2$—NH—Arg$^9$] bradykinin and desArg9-bradykinin. A preferred analog is known as RMP-7 or A-7 and is identified in U.S. Pat. No. 5,268,164 and PCT Application No. WO 92/18529. RMP-7 was supplied by Alkermes, Inc. (Cambridge, Mass.).

The amount of bradykinin or bradykinin analog which is infused into the carotid artery in order to selectively open the abnormal brain tissue capillaries to allow passage of neuropharmaceutical agents through the BBB may be varied depending upon the particular abnormal tissue being treated and the patient weight. The preferred dosage ranges from between 0.05 μg/kg body weight/minute to about 20 μg/kg body weight/minute. The total amount of bradykinin or bradykinin analog which is infused into the carotid artery during any single treatment is preferably kept below about 400 μg/kg body weight. For treating most abnormal tissues, the rate at which bradykinin or bradykinin analog is infused into the carotid artery will be on the order of about 10 μg/kg body weight/minute.

It is preferred that the bradykinin or bradykinin analog is infused into the carotid artery over a relatively short time period on the order of about 5 minutes to about 20 minutes. The selective opening of the abnormal brain tissue capillaries resulting from the infusion lasts for approximately 20 minutes after the bradykinin or bradykinin analog is administered. During this time period, a neuropharmaceutical agent may be introduced intravenously or also through the carotid artery. The selectively open abnormal brain tissue capillaries allow passage of the neuropharmaceutical agent into the abnormal brain tissue for treatment.

Any of the well known neuropharmaceutical agents may be administered in accordance with the present invention. Low molecular weight (100–20,000) as well as high molecular weight (about 20,000 to 70,000) neuropharmaceutical agents may be used. In addition to neuropharmaceutical agents, diagnostic agents may be used including imaging or contrast agents. Exemplary diagnostic agents include substances that are radioactively labelled such as 99-Tc glucoheptonate, gallium-EDTA, ferrous magnetic or iodinated contrast agents. Exemplary neuropharmaceutical agents include antibiotics, adrenergic agents, anticonvulsants, nucleotide analogs, chemotherapeutic agents, antitrauma agents and other classes of agents used to treat or prevent neurological disorders. Specific neuropharmaceutical agents which can be administered into abnormal brain tissue in accordance with the present invention include cisplatin, carboplatin, tumor necrosis factor-$\alpha$ (TNF-$\alpha$), methotrexate, 5-FU, amphotericin, immunotoxins, boron compounds, monoclonal antibodies and cytokines, such as interferons, interleukins, transforming growth factors, oligonucleotides.

The bradykinin or bradykinin analog is administered into the carotid artery by any of the well known infusion techniques. For example, the bradykinin or bradykinin analog may be directly infused into the carotid artery by the following preferred procedure used for cerebral angiography where a catheter is inserted into the femoral artery directed using fluoroscopic X-rays into the internal carotid artery or a more distal cerebral artery.

The bradykinin or bradykinin analog is preferably infused in the form of a pharmaceutical solution dissolved in 0.9% saline at a concentration of approximately 10–40 µg/ml. Any of the well known pharmaceutical carders may be used as a diluent for the bradykinin or bradykinin analog to provide a solution which can be infused directly into the carotid artery.

Although the present invention is applicable to selectively treating a wide variety of abnormal brain tissues, the following examples will be limited to a demonstration of the invention with respect to brain tumors, with it being understood by those skilled in the art that the invention is not so limited.

Examples of practice are as follows.

EXAMPLE 1

Bradykinin

An experimental brain tumor model was made using female Wistar rats and RG-2 glioma cells. The RG-2 glioma cell line was maintained in a monolayer culture in F12 medium with 10% calf serum. Female Wistar rats, each weighing 150 to 250 gm were anesthetized with intra peritoneal pentobarbital (30 mg/kg). Glial tumors were implanted into the right hemisphere by intracerebral injections of $1 \times 10^5$ RG-2 glioma cells in five µl of 1.2% methyl cellulose (F12 medium). One week after tumor implantation, the rats were used for the brain tumor model.

The rats were divided into two groups: a bradykinin group treated with intracarotid infusion of 10 microliters/kg/min of bradykinin or the control group treated with intracarotid infusion of saline. The effect of intracarotid infusion of bradykinin was compared to saline infusions by statistical analysis of the Ki values using ANOVA and Students T-Tests.

It was determined that the 10 µ/kg/min dose of bradykinin dissolved in 0.9% saline did not alter systemic blood pressure. At infusion rates greater than 20 µg/kg/min the systemic blood pressure in the rats was reduced.

The blood volume for the quantitative examination of permeability was calculated with a graphic method using [$^{14}$C] dextran (MW 70,000). The blood volume in normal brain tissue and tumors were 4.5 and 9.15 µ/g, respectively (FIG. 1). The slopes were the unidirectional transfer constants, the Ki values (µl/g/min), in the two groups. The slope of the line of the rats treated with bradykinin indicated that the increased volume of distribution resulted from increased permeability and not from increased blood volume. The tumor blood volume was almost twice that of the normal brain tissue, but the brain and tumor blood volumes were not altered by intracarotid bradykinin infusion.

Figure 2A:
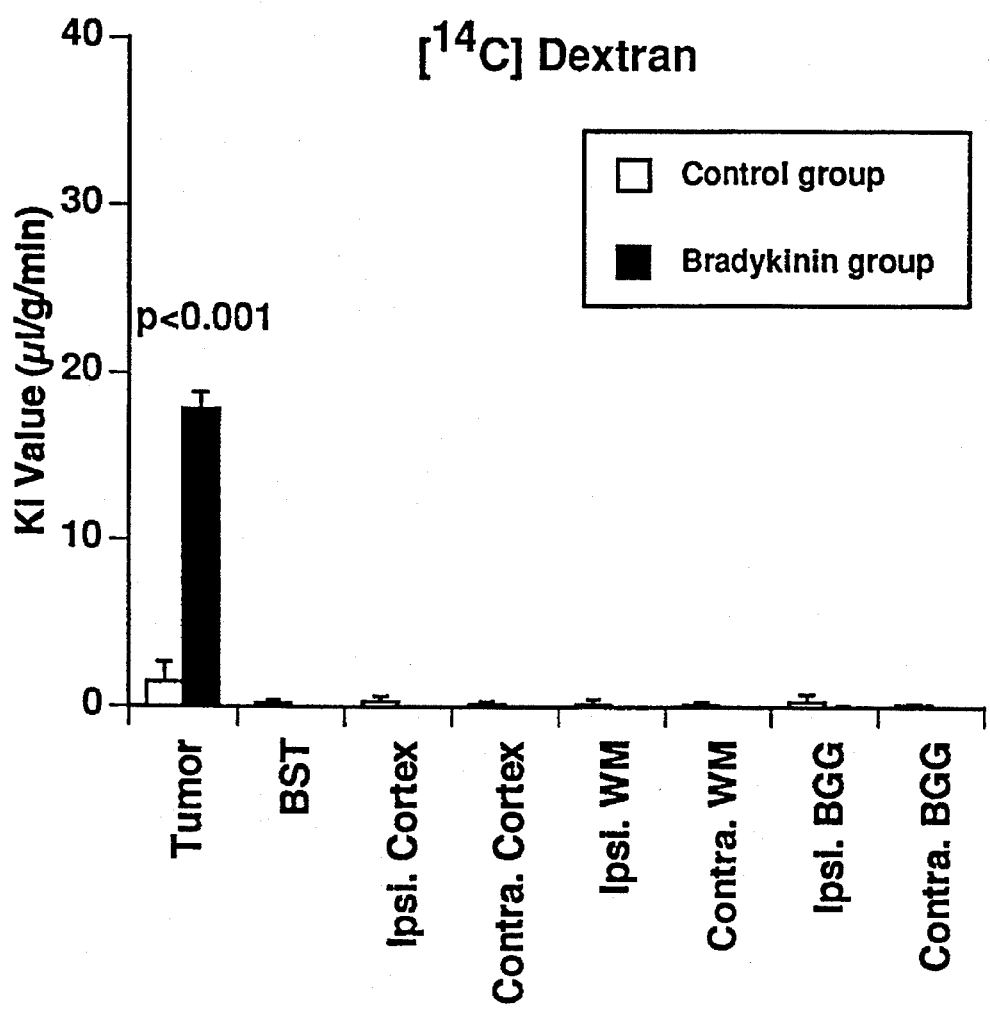
FIG. 2A is a graph which summarizes test results showing the selective uptake of dextran by brain tumor tissue in accordance with the method of the present invention. Bradykinin or a bradykinin analog selectively increased permeability within the tumor 12-fold without increasing permeability in brain surrounding tumor (BST), ipsilateral normal cortex (ipsi cortex) contralateral normal cortex (contra cortex) ipsilateral white matter (ipsi wm) contralateral white matter (contra wm) or ipsilateral or contralateral basal ganglia (BGG).

[$^{14}$C] AIB and [$^{14}$C] dextran were used for quantitative autoradiographic examination of regional permeability. One week after tumor implantation, the rats were again anesthetized and a polyethylene (PE-10) catheter was inserted retrograde throughout the external carotid artery to the common carotid artery bifurcation ipsilateral to the tumor. The external carotid artery was then ligated. One femoral artery was cannulated to monitor systemic blood pressure and the other femoral artery was cannulated to withdraw arterial blood. Body temperature was maintained at 30° C. and arterial blood gas levels, blood pressure, hematocrit were monitored. Animals with abnormal physiological parameters were eliminated. After rat preparation, bradykinin (10 µg/kg/min in saline) or saline as control was infused into the right carotid artery at a rate of 53.3 µ/min for 15 minutes. Five minutes after the start of the intracarotid infusion, 100 µCi/Kg of the tracer was injected as an intravenous bolus. A peristaltic withdrawal pump was used to withdraw femoral arterial blood at a constant rate of 0.083 ml/min immediately after injection of tracer for determination of serum radioactivity. Fifteen minutes after the start of intracarotid infusions, the animals were killed by decapitation and the brains were rapidly removed and frozen. The regional permeability in the brains and tumor tissues were expressed by the unidirectional transfer constant, Ki value (µl/g/min). The Ki value of the tumors for [$^{14}$C] dextran (MW 70,000 in the bradykinin group was 12-fold higher than that for the control group (Mean±SD; 17.84±1.00 vs. 1.47±1.24; $p<0.001$) (FIG. 2A). This Ki value corresponded well with the Ki value derived from the slope in FIG. 1.

Figure 2B:
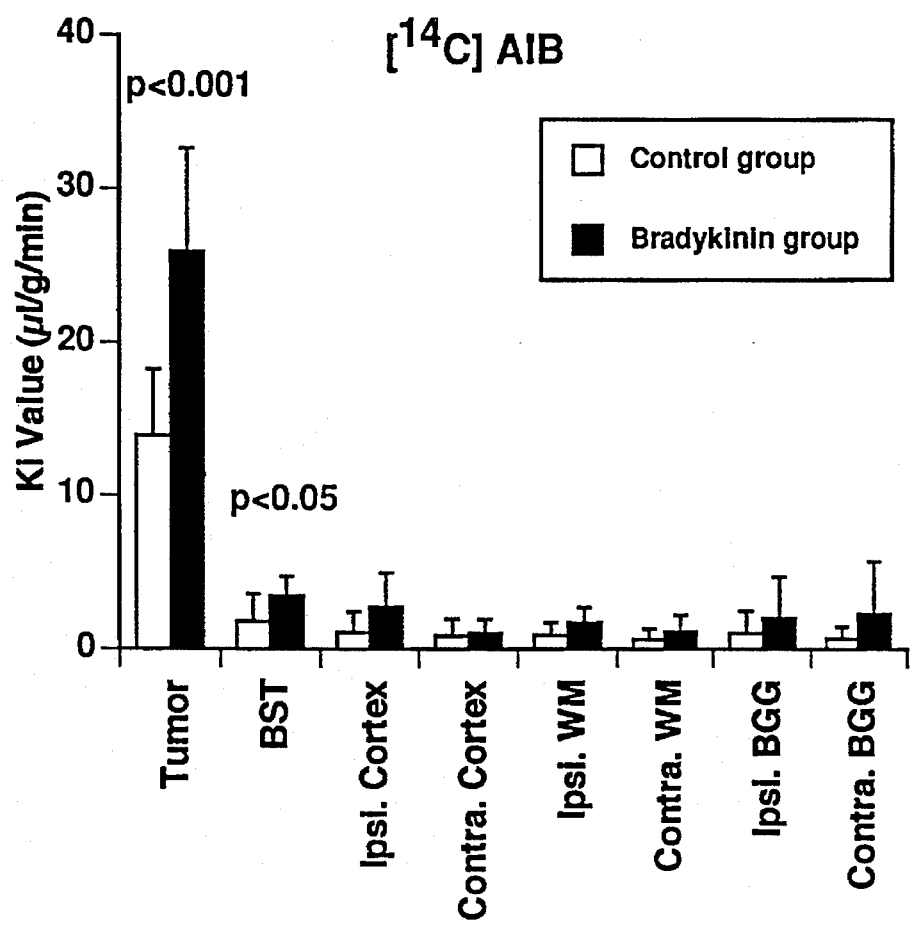
FIG. 2B depicts test results showing selective uptake of AIB by brain tumor tissue in accordance with the method of the present invention. In contrast to dextran, which has a molecular weight of 70,000, AIB has a molecular weight of 100.

The Ki values of brain regions without tumor in either bradykinin treated or control groups were very low and there was no significant differences between the two groups. The Ki value of the tumors for [$^{14}$C] AIB (MW 103) in the bradykinin group was 1.8-fold higher than that for the control group (25.91±6.78 vs. 13.95±4.29; $p<0.001$ (FIG. 2B). The Ki value of the brain surrounding tumor (BST; areas at 2 mm distance from the border of the tumor) for [$^{14}$C] AIB for the bradykinin group was also higher than that for the control group (3.50±1.29 vs. 1.83±1.78; $p<0.05$). This result shows that the effect of bradykinin on brain tumor capillaries is selective and the effect is more profound as the size of the tracer molecule increases.

Bradykinin has a short biological half-life because of its proteolytic inactivation (17). To determine the duration of the bradykinin effect on tumor capillary permeability, the Ki at three different time periods was measured. The rat preparation was the same as described above. The Ki value was measured in three different periods by changing the time of [$^{14}$C] dextran injection as also previously described. The three periods were as follows: 0 to 10 minutes during the intracarotid bradykinin infusion, 0 to 10 minutes after the infusion, and 10 to 20 minutes after the infusion. The experiment was terminated at the end of each period. The Ki value was calculated.

Autoradiography was conducted as follows: the frozen brains were mounted onto pedestals with M-1 embedding matrix, and 20 µm coronal sections were cut into a cryotome. The sections were thawmounted onto cover slips, and autoradiograms were generated by coexposing the sections on Kodak XAR-5 film with tissue-calibrated $^{14}$C standards for 2 weeks. The sequential section was stained with hematoxylin for correlation of areas of histologically verified tumor with autoradiograms. The regional radioactivities were measured in tumor, brain surrounding the tumor (BST; areas at around 2 mm distance from the border of the tumor), ipsilateral cortex to tumor (ipsi cortex), contralateral cortex (contra cortex), ipsilateral white matter (ipsi WM), contralateral WM (contra WM), ipsilateral basal ganglia (ipsi BGG), and contralateral BGG (contra BGG). Quantitative analysis of the regional radioactivity was performed using a computer (Macintosh II) with a scanner (UMAX $UC_{630}$) and the software, Image 1.45 (NIH).

Figure 3:
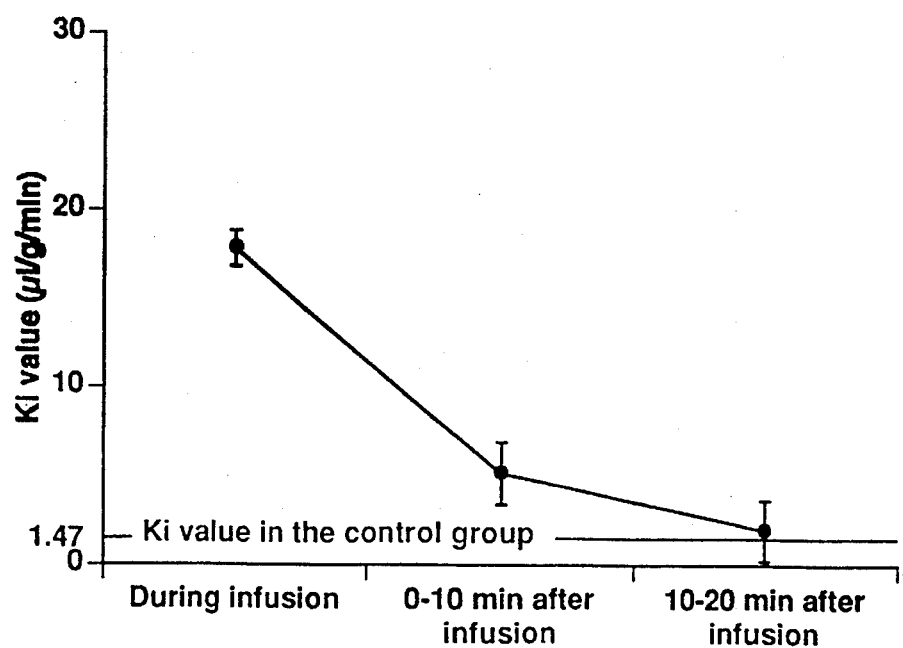
FIG. 3 depicts test results showing the decrease in blood-tumor barrier permeability during the time period following infusion of bradykinin or a bradykinin analog into the carotid artery in accordance with the present invention. The effect is reversible approximately 20 minutes after stopping the infusion of bradykinin or a bradykinin analog.

The effect of bradykinin on tumor permeability was diminished 20 minutes after stopping the intracarotid bradykinin infusion (FIG. 3). The degradation of bradykinin in rats has been reported to be on the order of several hours (18). The shorter effect of bradykinin on tumor capillary permeability is believed to be due to both the selective intracarotid infusion and the lower dose of bradykinin used. The short effect on tumor capillaries of intracarotid infusion of bradykinin is desirable for the selective delivery of anticancer drugs in the treatment of the brain tumors.

The enzyme that degrades bradykinin is peptidyl carboxypeptidase kinase II, which is identical to angiotensin I converging enzyme (ACE) (19). Williams, et al., using antiserum to the purified pig kidney ACE, reported that the pig brain capillary contained ACE (20). Moreover, the ACE inhibitor, captopril, enhanced the bradykinin effect (14, 21). Whether the rat brain capillary had ACE was examined using antiserum to the purified human kidney ACE. Angiotensin converting enzyme was not recognized in the rat brain capillaries, whereas this antiserum recognized ACE in the rat kidney cortex. When an intravenous captopril infusion was used to enhance the effects of bradykinin on tumor permeability, hypotension occurred which made it difficult to maintain normal systemic pressure.

Microscopic analysis was performed using intravenously injected horseradish peroxidase (HRP) as described in (22). After rat preparation as previously described, bradykinin (10 μg/kg/min in saline) or saline as a control was injected into the fight carotid artery for 15 minutes. Five minutes after the start of the intracarotid infusion, 20 mg/100 g of horseradish peroxidase (HRP) was injected by an intravenous bolus. Ten minutes after the HRP injection, rats were perfused with a mixture of 2% glutaraldehyde and 2% formaldehyde in 0.1 sodium phosphate buffer solution at pH 7.4 through the heart. After fixation, the brains were removed and cut at 40 μm thickness on a vibratome. The sections were preincubated for 15 minutes at room temperature in the medium consisting of 10 ml 0.05 M-Tris-HCl buffer (pH 7.4), 3,3'-diaminobenzidine tetrahydrochloride and 0.02% hydrogen peroxide (Sigma). The sections were trimmed down to the areas of interests, post-fixed for 2 hours in 2% osmium tetroxide with 0.1M sodium phosphate, dehydrated, and embedded in plastic. Plastic sections 1 μm thick were observed under light microscopy.

The HRP stain was well recognized in the extracellular space between tumor cells in the bradykinin group, whereas the HRP stain was much less in the control group. In normal brain, bradykinin increased the HRP staining within the cytoplasm of only a few endothelial cells and there was no extravasation of HRP between cells. The effect of low dose bradykinin on endocytosis in endothelial cells in normal brain is, therefore, small. It has been reported that the nanomolar concentrations of bradykinin stimulated the uptake of the fluorescent marker, Lucifer yellow, in the brain capillary endothelial cells by 40% (23). It also has been reported that high dose intracarotid infusion of bradykinin (almost 6 times higher than the dose of the present invention) caused intravasation of HRP around the normal brain capillary. Vasodilatation of microvessels and HRP endocytosis in endothelial cells was also recognized. The fight junctions of the endothelium were intact (16). In the above example, the HRP stain was limited to a few endothelial cells in the bradykinin group. This demonstrates that in contrast to other studies using high dose bradykinin, lower doses of bradykinin in accordance with the present invention selectively increase the tumor permeability without increasing the normal brain permeability.

To demonstrate that bradykinin could selectively deliver other high molecular weight compounds into tumors, Evans blue (EB) was injected intravenously instead of radiolabeled tracers as follows: after the preparation of rats as previously described, 2 ml/kg of 2% Evans Blue was injected intravenously as also described above. After the intracarotid bradykinin infusion, the rat was perfused with 200 ml of phosphate buffer through the heart to wash out the remaining EB from the vessels. The brains were removed immediately and cut as coronal sections.

Since EB binds to serum albumin (MW 67,000) in blood and distributes with albumin in vivo, EB staining in the tissue indicates the distribution of albumin (4). In order to observe the extravasated EB and not the EB remaining in the vessels in the brain, the blood from the brain was washed out by perfusing the rats with phosphate buffer from the heart. The EB staining was well recognized in the tumor but not in the normal brain of the bradykinin group. Much less staining was seen in the control group. This shows that intracarotid bradykinin infusion selectively increased the delivery of EB albumin to the tumor.

The above example demonstrates the use of intracarotid bradykinin infusion as a method to selectively deliver high molecular weight agents to brain tumors. Intracarotid bradykinin infusion at low doses increases the permeability for the high molecular weight tracer dextran by 12-fold, and for low molecular weight tracer AIB by 1.8 fold. Moreover, selective extravasation of HRP and EB staining in tumors were caused by intracarotid bradykinin infusion. Accordingly, the method of the present invention is useful for selectively delivering both low and high molecular weight compounds to brain tumors.

EXAMPLE 2

Bradykinin Analog—RMP-7

In this example, the bradykinin analog, RMP-7, was investigated for its ability to selectively increase uptake of molecular tracers in RG2 glial tumors. As will be shown below, RMP-7, infused in low doses (0.1 μg/kg/min) through the intracarotid artery ipsilateral to RG2 gliomas in rats, significantly increased the permeability in tumor capillaries to methotrexate and to four other tracers of varying molecular weights, compared to intracarotid infusion of vehicle alone. Tracers used to examine permeability included radiolabeled alpha-aminoisobutyric acid (AIB) (MW 103 daltons), sucrose (MW 342 daltons), methotrexate (MW 454.5 daltons), inulin (MW 5000 daltons), and dextran (MW 70,000 daltons). Permeability was expressed as the unidirectional transfer constant, $K_i$ (μg/g/min). The permeability ($K_i$) of tumors in the RMP-7 group vs. vehicle control group were as follows: AIB=35.3±9.11 vs. 12.7±4.56 ($p<0.01$); sucrose=16.5±3.83 vs. 9.28±3.12 ($p<0.01$); methotrexate= 26.3±10.3 vs. 8.98±6.78 ($p<0.05$); inulin=13.5±3.23 vs. 6.55±4.32 ($p<0.01$); dextran=15.2±3.42 vs. 1.47±1.24 ($p<0.001$). Permeability of RG2 gliomas to high molecular weight dextran (70,000) was 10.3-fold higher in the RMP-7 group and did not significantly increase the blood volume in tumor or brain tissue. The permeability of normal brain capillaries was unaffected by intracarotid infusion of 0.1 μg/kg/min RMP-7.

Female Wistar rats, weighing 150 to 200 gm, were used for this study. The bradykinin analog, RMP-7, was supplied by Alkermes (Cambridge, Mass.) Evans Blue (EB), was obtained from Sigma. Alpha-[1-$^{14}$C]-aminoisobutyric acid (AIB) (57.6 mCi/mmol), Carboxyl-[$^{14}$C] dextran (0.81 mCi/g), and [3H] methotrexate (38.3 Ci/mmol) were obtained from New England Nuclear. [$^{14}$C] sucrose (363 mCi/mmol) and [$^{14}$C] inulin (3.15 μCi/mg) were obtained from ICN (Costa Mesa, Calif.).

The RG2 glioma cell line was maintained in a monolayer culture in F12 medium with 10% calf serum. The rats were anesthetized with intraperitoneal pentobarbital (30 mg/kg). Glial tumors were implanted into the right hemisphere by intracerebral injections of 1×10$^5$ RG2 glioma cells in 5 μ of (1.2% methylcellose) F12 medium by a Hamilton syringe. The coordinates used were 5 mm lateral to the bregma, 2 mm anterior to the coronal plane and 4.5 mm deep to the dural surface.

One hundred and sixteen rats were used in this example. Rats were divided into two major groups; a treatment group administered intracarotid infusion of 0.1 μg/kg/min of RMP-7 for 15 minutes or a control group similarly administered intracarotid infusion of vehicle.

One week after tumor implantation, the rats were again anesthetized and a polyethylene (PE-10) catheter was inserted retrograde through the external carotid artery to the common carotid artery bifurcation ipsilateral to the tumor. The external carotid artery was then ligated. One femoral artery was cannulated to monitor systemic blood pressure and the other femoral artery was cannulated to withdraw arterial blood. Body temperature was maintained at 37° C. and arterial blood gases, blood pressure, and hematocrit were monitored. Animals with abnormal physiological parameters were eliminated.

RMP-7 (at 1.5 μg/kg) or vehicle (control) was infused into the right carotid artery at a volume rate of 0.8 ml over 15 minutes (i.e. 53 μ/min). In blood volume studies, 100 μCi/kg of [$^{14}$C] dextran was injected as an intravenous bolus at either 5, 10, 14 or 14.5 minutes after the start of the intracarotid infusion to make the circulation time of dextran 10, 5, 1, 0.5 minutes, respectively. In regional permeability studies, 5 minutes after the start of the intracarotid infusion, 100 μCi/kg of the tracer was injected as an intravenous bolus. A peristaltic withdrawal pump was used to withdraw femoral arterial blood at a constant rate of 0.083 ml/min immediately after the injection of the tracer for the determination of serum radioactivity. Fifteen minutes after the start of intracarotid infusions, the animals were killed by decapitation and the brains were rapidly removed and frozen.

The frozen brains were mounted onto pedestals with M-1 embedding matrix, and 20 μm coronal sections were cut with a cryotome. The sections were thaw-mounted onto cover slips, and autoradiograms were generated by co-exposing the sections on Kodak XAR-5 film with tissue-calibrated $^{14}$C standards for 2 weeks. The sequential section was stained with hematoxylin for correlation of areas of histologically verified tumor with autoradiograms. The regional radioactivity was measured in tumor, brain surrounding the tumor (BST; areas within 2 mm distance from the border of the tumor), ipsilateral cortex to tumor, contralateral cortex, ipsilateral white matter (WM), contralateral WM, ipsilateral basal ganglia (BG), and contralateral BG. Quantitative analysis of the regional radioactivity was performed using a computer (Macintosh II) with a scanner (UMAX UC630) and the software, Image 1.45 (NIH). The effect of intracarotid infusion of RMP-7 was compared to vehicle infusion by statistical analysis of the Ki values using ANOVA and Student's t-test.

Six rats were used to examine whether RMP-7 could selectively deliver albumin to tumors. Evans blue (EB) was injected intravenously instead of radiolabeled tracers. After the preparation of rats, 2 ml/kg of 2% EB was injected intravenously instead of radiolabeled tracers. After the intracarotid RMP-7 (n=3) or vehicle (n=3) infusion, the rat was perfused with 200 ml of phosphate buffer through the heart to wash out the remaining EB from the vessels. The brains were removed immediately and cut as coronal sections.

RMP-7 infused at a rate greater than 1.0 μg/kg/min (dissolved in phosphate buffer, pH 7.4) reduced systemic blood pressure in rats when given either intravenously or into the carotid artery. The 0.1 μg/kg/min rate of intracarotid RMP-7 infusion used in quantitative experiments did not alter systemic blood pressure. Physiological parameters, which included arterial blood pH, PaO$_2$, were also monitored. These physiological parameters were not significantly changed by RMP-7 infusion at a rate of 0.1 μg/kg/min.

Figure 4:
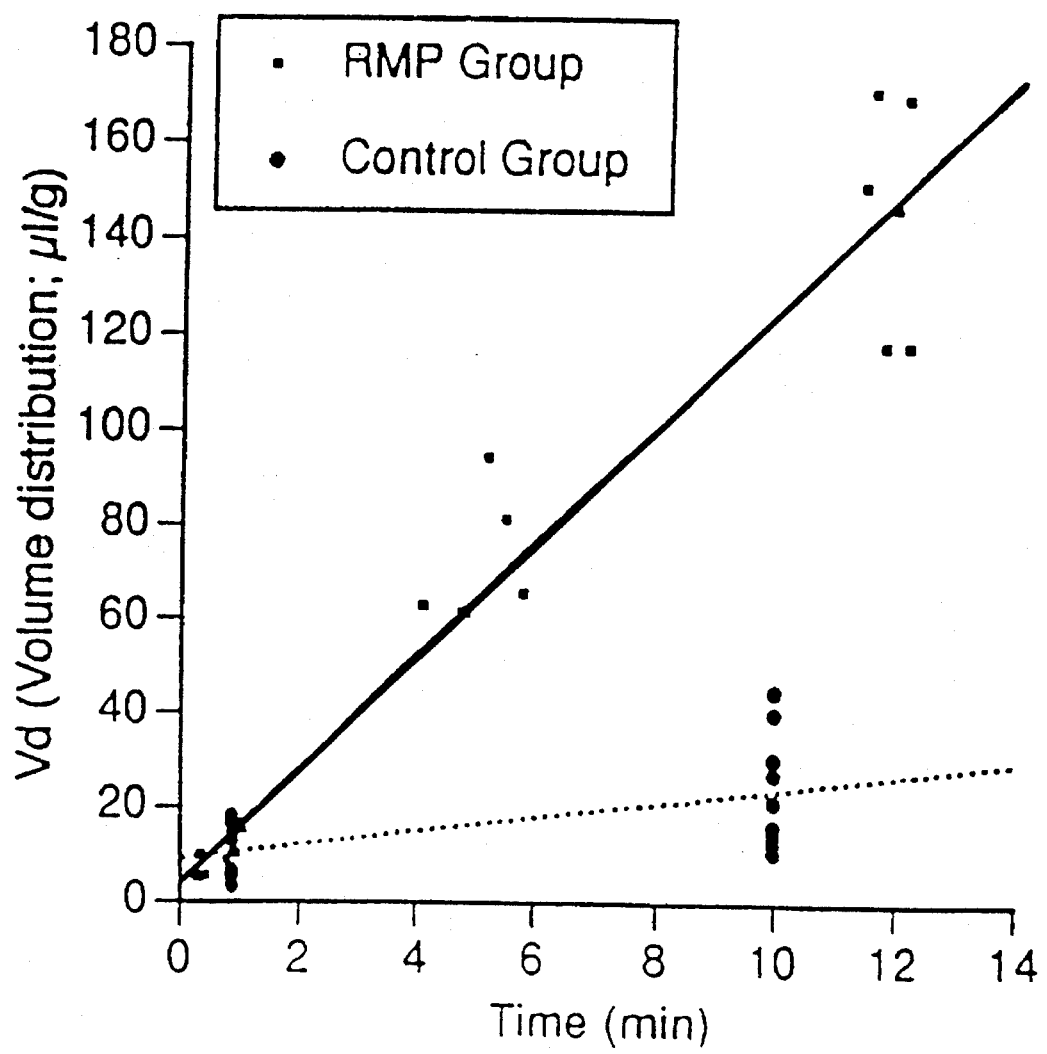
FIG. 4 is a graph showing the results of a determination of blood volume in experimental brain tumors. Data was obtained from quantitative studies by changing the experimental duration of RMP-7 infusion to 0.5, 1, 5, and 10 min. By plotting the value of the volume distribution (Vd μ/g) and the value of the tracer concentration in tissue divided by the tracer concentration in the blood, the regression line was obtained. The slope of the lines indicates unidirectional transfer constant (Ki (μl/g/ml) and the y-intercept of the lines indicates the blood volume in the tissue. Based on the slope of the solid line (RMP-7 group) the Ki value in tumors to [$^{14}$C] dextran in the RMP-7 group is 17.9 μ/kg/min. Intracarotid RMP-7 infusion changed permeability in the tissue but not blood volume. The blood volume in the tumor was 9.4 μ/g. The average blood volume in the brain was 3.7 μ/g.

The blood volume for the quantitative examination of permeability was calculated with a graphic method using [$^{14}$C] dextran. The blood volume in brain and tumor tissue were 3.7 and 9.4 μl/g, respectively (FIG. 4). The slope is the unidirectional transfer constant Ki (μl/g/min). Ki was similar in these experiments whether calculated using the graphic method or the method described by Ohno (25) and Ziylan (26). The Y intercept of the lines indicates that the increased volume of distribution after RMP-7 infusion results from increased permeability and not from increased blood volume. The tumor blood volume was almost twice that of the brain, but the brain and tumor blood volumes were not significantly altered by intracarotid RMP-7 infusion.

Figure 5A:
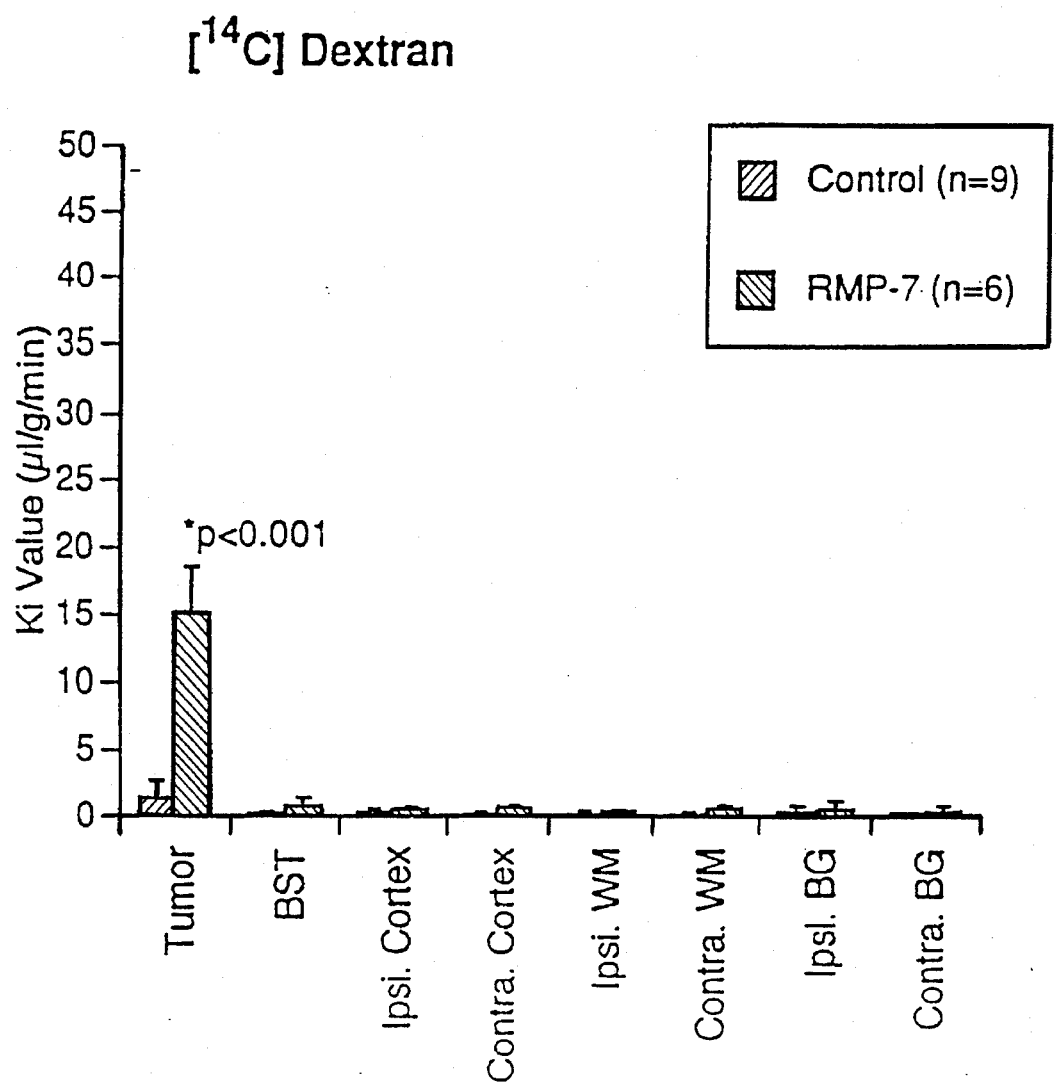
Figure 5B:
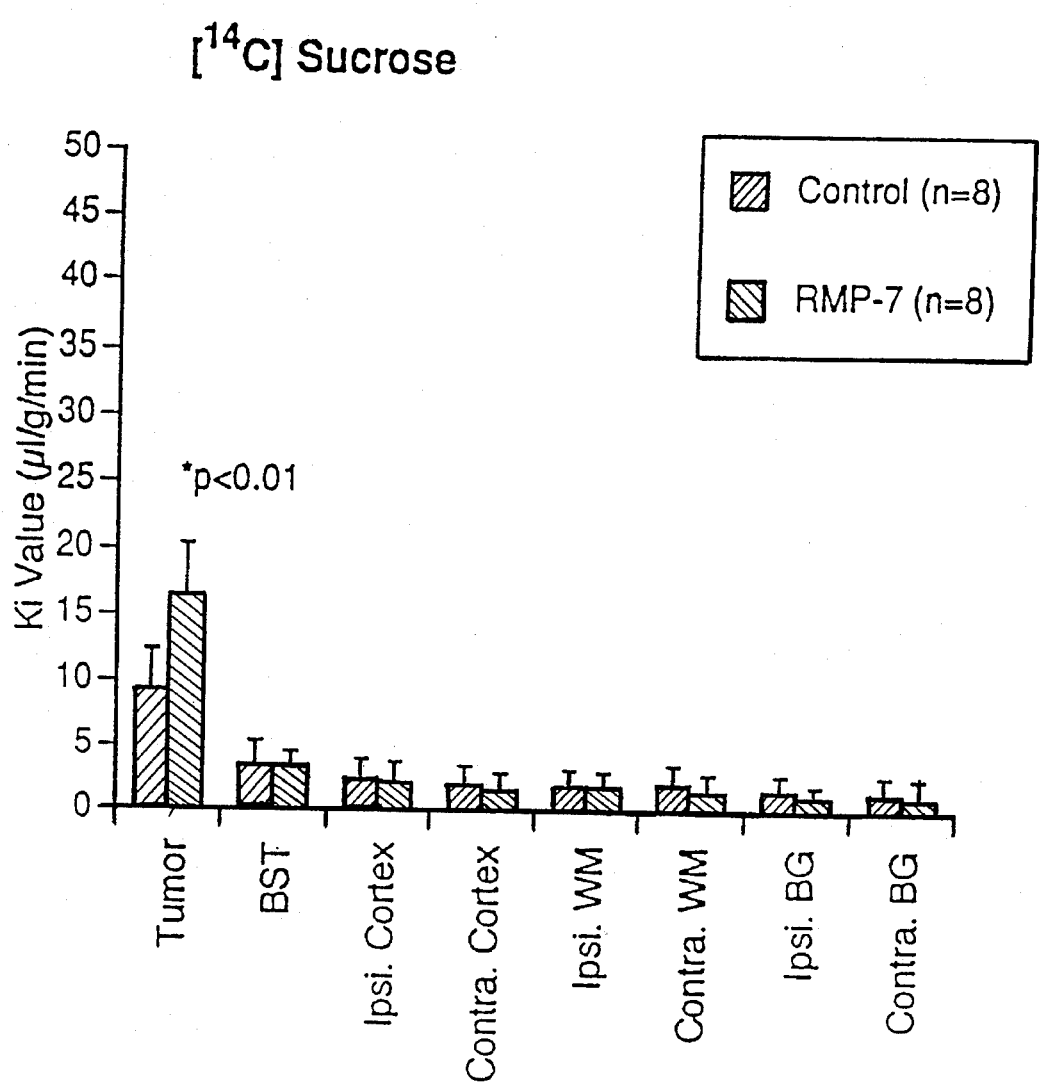
Figure 5C:
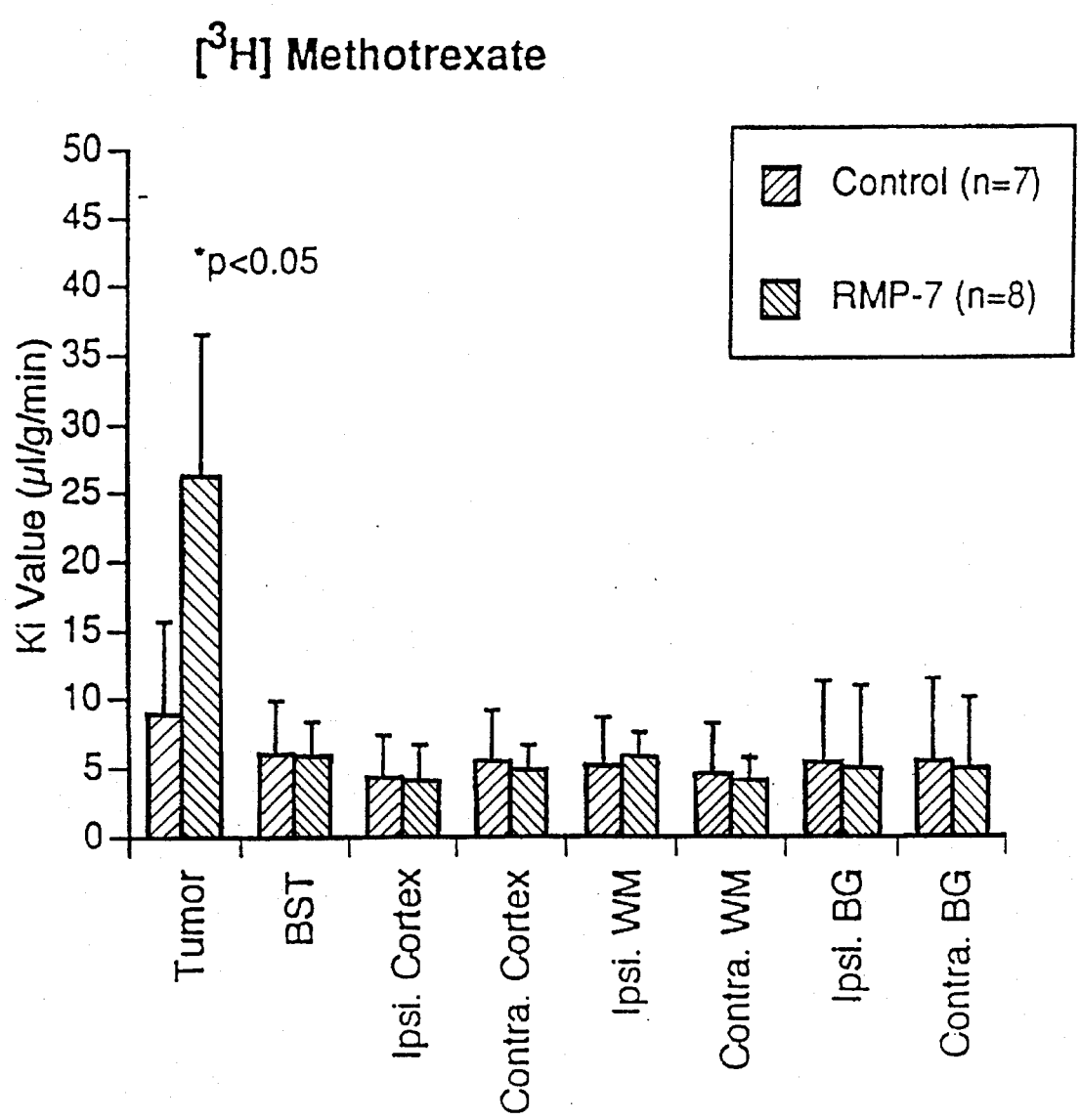
Figure 5D:
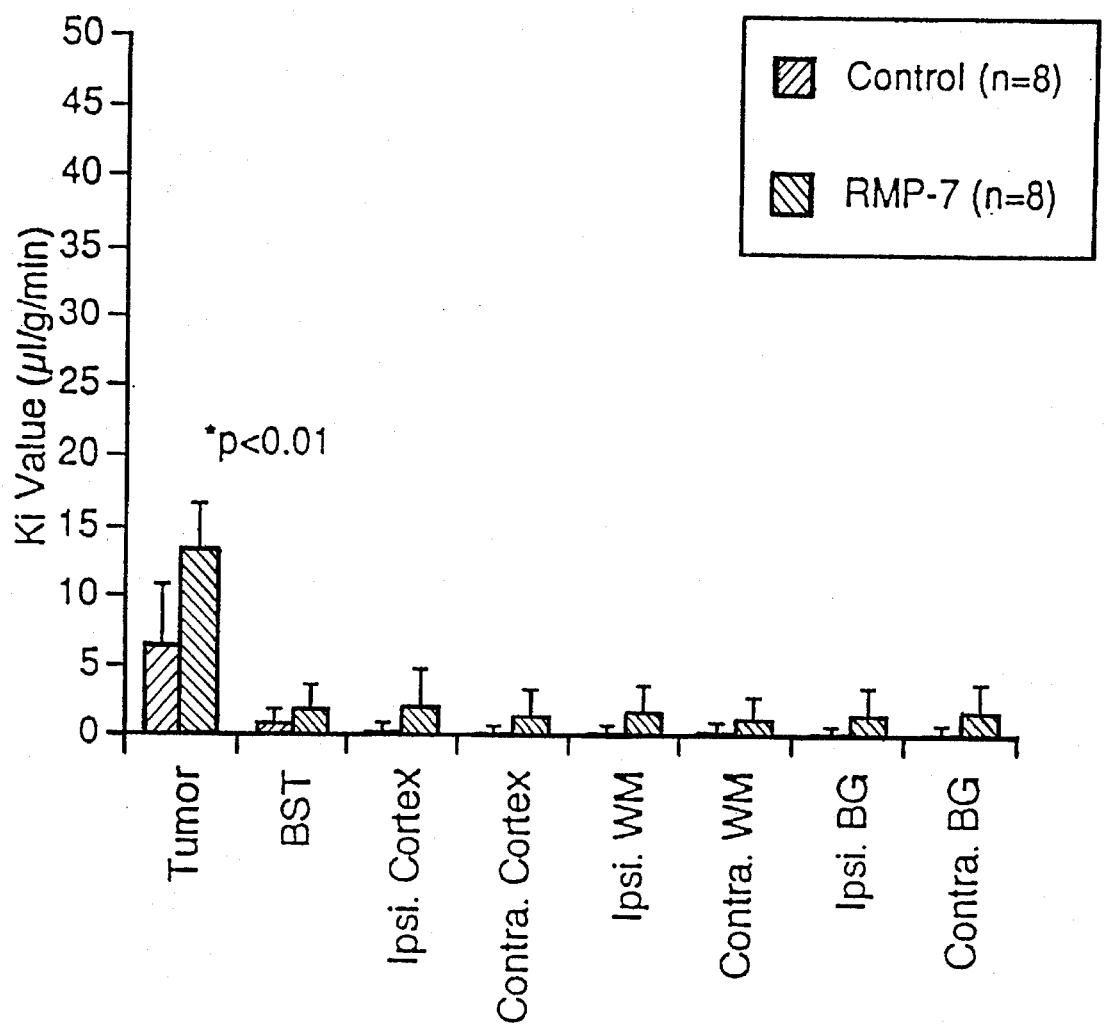

The permeability (Ki) in tumors to [$^{14}$C] dextran (MW 70,000) after RMP-7 infusion (n=6) was 10.3-fold higher than in controls (n=9) (Mean±SD; 15.2±3.42 vs. 1.47±1.24; p<0.001) (FIG. 5A). The Ki values were calculated using the method of Ohno (25) and Ziylan (26). The Ki values calculated above corresponded well with the Ki value derived from the graph in FIG. 4. The permeability of the tracers in tumors after RMP-7 infusion vs. vehicle was consistently greater, including [$^{14}$C] AIB (MW 103) (35.3±9.11, n=8 vs. 12.7±4.56, n=11; p<0.01) [$^{14}$C] sucrose (MW 342) (16.5±3.83, n=8 vs. 9.28±3.12, n=6; p<0.01), $^3$H methotrexate (MW 454.5) (26.3±10.3, n=8 vs. 8.98±6.78, n=7; p<0.05), and [$^{14}$C] inulin (MW 5000) (13.5±3.23, n=8 vs. 6.55±4.32, n=8; p<0.01) (FIGS. 5B, 5C, 5D and 5E).

Brain within 2 mm of tumors was evaluated as brain surrounding tumor (BST), since this tissue may be affected by tumor compression and vasoactive compounds released by the tumor itself. The Ki to brain within 2 mm of tumor for [$^{14}$C] AIB after RMP-7 infusion was higher than after control infusion (6.62±2.35, n=8 vs. 1.48±1.71, n=1 1; p<0.05). The Ki of dextran, inulin and sucrose was not, however, significantly increased in brain within 2 mm of tumors after RMP-7 infusion. RMP-7 infusion did not increase permeability in any normal brain region more than 2 mm from tumor to any of the tracers tested. At the dose tested, RMP-7 infusion selectively increased permeability in tumors to tracers of varying size, but did not increase permeability in normal brain. Permeability was also increased to AIB in brain within 2 mm of tumor after RMP-7 infusion.

Figure 6:
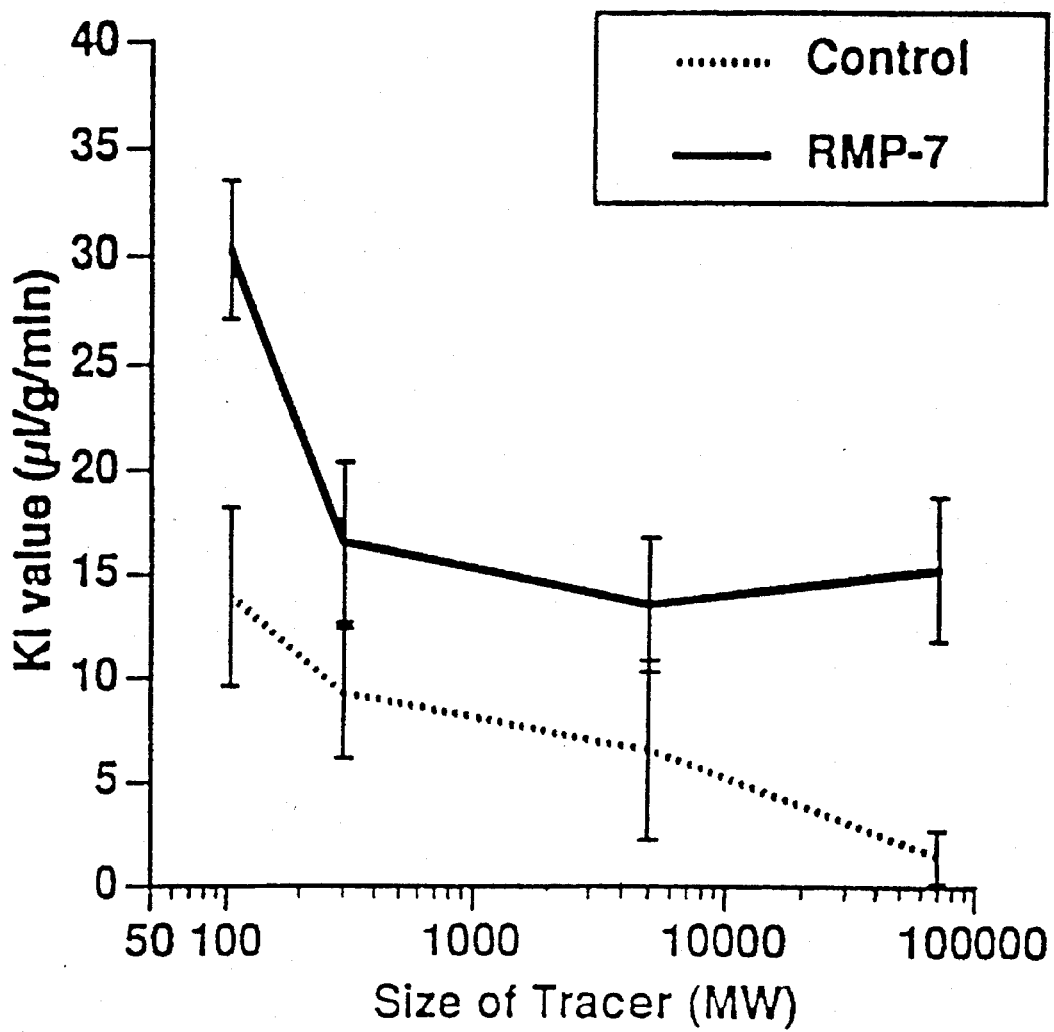
FIG. 6 is a graph depicting Ki values (μg/g/min) within RG2 tumors comparing Ki to size of tracers with and without intracarotid RMP-7 infusions. The values are shown as the mean±SD. The Ki values of the control group showed a general decline with increasing molecular weight of radio-labeled tracers. The Ki values in the RMP-7 group are significantly higher than those of the control group. There was also a decline in Ki with RMP-7 between AIB and the other tracers.

When the Ki in tumors for all tracers were plotted against the size of the tracers after vehicle infusion, a general decline in Ki was observed as the molecular weight of radiolabeled tracers increased (FIG. 6). The Ki in tumors after RMP-7 infusion also showed a decline with increasing molecular weight of tracers, but the slope of the decline after RMP-7 infusion was much less than that in the control group. The relative effect of RMP-7 on increasing permeability, therefore, is much greater as the size of the tracer increases.

Evans Blue staining was well recognized in tumor but not normal brain tissue after RMP-7 infusion. However, less staining was seen in tumors from control rats, whereas intracarotid RMP-7 infusion selectively increased the delivery of Evans Blue-bound albumin to tumors.

Intracarotid infusion of RMP-7 selectively increased permeability in brain tumors to [$^{14}$C] AIB, [$^{14}$C] sucrose, [3H] methotrexate, [$^{14}$C] inulin, and [$^{14}$C] dextran by 2.8, 1.8, 3.9, 2.1, and 10.3 fold, respectively. The molecular weights of most antitumor compounds range from 100 to 40,000 daltons. Most antitumor agents are, therefore, within the molecular weight range of the tracers used in this study. High molecular weight agents, which are the most difficult to deliver to brain tumors, are the compounds most beneficially affected by RMP-7 opening of the blood-tumor barrier.

EXAMPLE 3

Carboplatin And TNF-α With RMP-7

This example was conducted in the same manner as Example 2, except that carboplatin and tumor necrosis factor-α (TNF-α) were used in place of AIB, sucrose, methotrexate, inulin and dextran.

Figure 7:
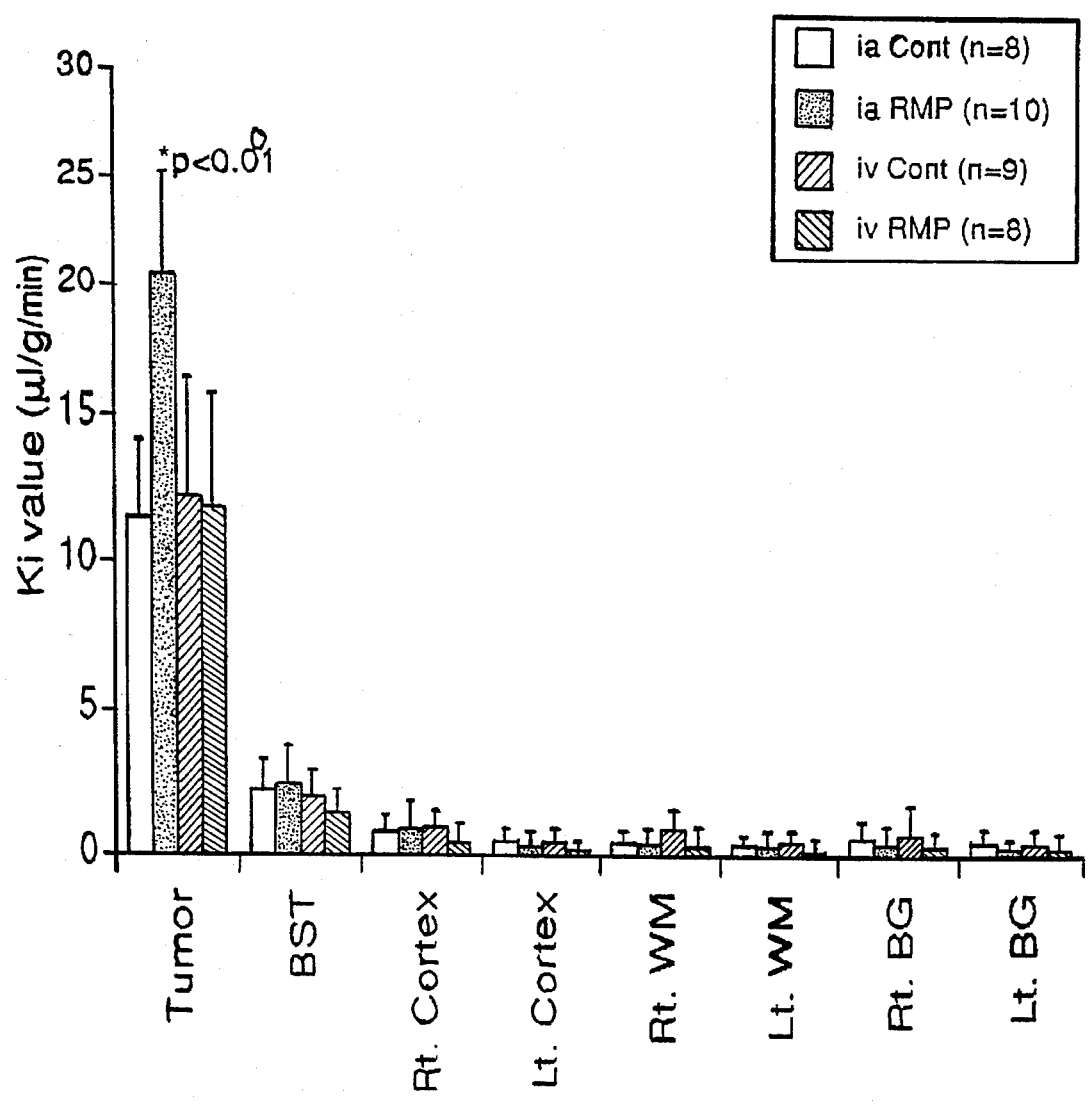
FIG. 7 shows the regional Ki values of [$^{14}$C] carboplatin when administered with the bradykinin analog RMP-7 in accordance with the present invention.
Figure 8:
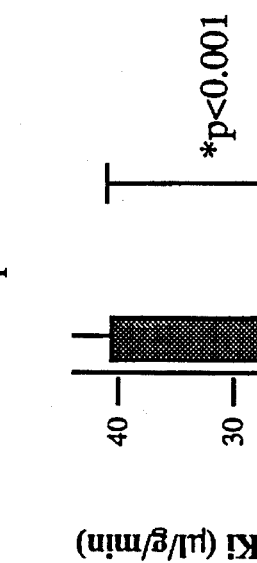
FIG. 8 shows the regional Ki values of [$^{125}$I] TNF-α when administered with the bradykinin analog RMP-7 in accordance with the present invention.

The results of carboplatin infusion with RMP-7 are shown in FIG. 7. The results of the TNF-α infusion with RMP-7 are shown in FIG. 8.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

BIBLIOGRAPHY

1. Kumagai, A. K., Eisenberg, J. B., Pardridge, W. M., "Absorptive-mediated endocytosis of cationized albumin and β-endorphin-cationized albumin chimeric peptide by isolated brain capillaries. Model system of blood-brain barrier transport," *J. Biol. Chem.* 262:15214–15219, 1987.

2. Neuwelt, E. A., Barnett, P. A., McCormick, C. I. et al., "Osmotic blood-brain barrier modification: monoclonal antibody, albumin, and methotrexate delivery to cerebrospinal fluid and brain," *Neurosurgery* 17:419–423, 1985.

3. Neuwelt, E. A., Hill, S. A., Frenkel, E. P., "Osmotic blood-brain barrier modification and combination chemotherapy: concurrent tumor regression in areas of barrier opening and progression in regions distant to barrier opening," *Neurosurgery* 15:362–366, 1984.

4. Pardridge, W. M., Kumagai, A. K., Eisenberg, J. B., "Chimeric peptides as a vehicle for peptide pharmaceutical delivery through the blood-brain barrier," *Biochem. Biophys. Res. Commun.* 146:307–313, 1987.

5. Iomiwa, K., Hazama, F., Mikawa, H., "Neurotoxicity of vincristine after osmotic opening of the blood-brain barrier," *Neuropathol. Appl. Neurobiol.* 9:345–354, 1983.

6. Black, K. L., Betz, A. L., Ar, D. B., "Leukotriene $C_4$ receptors in isolated brain capillaries," *Adv. Prostaglandin Thrornboxane Leukotriene Res.* 17:508–511, 1987.

7. Black, K. L., Hoff, J. T., "Leukotrienes and blood-brain barrier permeability," *Cereb Flow Metab.* 5 (Suppl):263–264, 1985.

8. Black, K. L., Hoff, J. T., "Leukotrienes increase blood-brain barrier permeability following intraparenchymal injections in rats," *Ann. Neurol.* 18:349–351, 1985.

9. Black, K. L., Hoff, J. T., McGillicuddy, J. E. et al., "Increased leukotriene $C_4$ and vasogenie edema surrounding brain tumors in humans," *Ann. Neurol.* 19:592–595, 1986.

10. Black, K. L., Chio, C. C., "Increased opening of blood-brain tumor barrier by leukotriene $C_4$ is dependent on size of molecules," *Neurological Res.* 74:402–404, 1982.

11. Black, K. L., King, W. A., Ikezaki, K., "Selective opening of the blood tumor barrier by intracarotid infusion of leukotriene $C_4$," *J. Neurosurg.* 72:9 12–916, 1990.

12. Baba, T., Black, K. L., Ikezaki, K., Chen, K., Becker, D. P., "Intracarotid infusion of leukotriene $C_4$ selectively increases blood-brain permeability after focal ischemia in rats," *J. Cereb. Blood Flow Metab.* 11, No. 4, 1991.

13. Chio, C. C., Baba, T., Black, K. L., "Selective blood-tumor barrier description by leukotrienes," *J. Neurosurg.* 77, 1992.

14. Yong, T. et al., *Circ. Res.* 70, 952, 1992.

15. Alvarez, A. L. et al., *Clin. Sci.* 82, 513, 1992.

16. Raymond, J. J., Robertson, D. M., Dinsdale, H. B., *Can. J. Neurol. Sci.* 13, 214, 1986.

17. Erdos, E. G., J. Cardiovasc. Pharmacol. 15, S20, 1990; Vanhoutee, P. M. et al., *Br. J. Clin. Pharmacol.* 28, 95, 1989.

18. Kumakura, S., Kamo, I., Tsurufuju, S., *Br. J. Pharmacol.* 93, 739, 1988.

19. Ng, K. K. F., Vane, J. R., *Nature* 216, 762, 1967.

20. Williams, T. A., Hooper, N. M., T. A. J., *J. Neurochem.* 57, 193, 1991.

21. Monbouli, J. V., Illiano, S., Nagao, T., Scott, B. T., Vanhoutte, P. M., *Circ. Res.* 71, 137, 1992.

22. Nishio, S., Ohm, M., Abe, M., Kitamura, K., *Acta. Neuropathol.* (Berl) 59, 1, 1983.

23. Guillot, F. L., Audus, K. L., *J. Cereb Blood Flow Metab.* 10, 827, 1990.

24. Dobbin, J., Crockard, H. A., Ross, R. R., *J. Cereb. Blood Flow Metab.* 9, 71, 1989.

25. Ohno, K., Pettigrew, K. O., Rapoport, S. T., "Lower limits of cerebrovascular permeability to nonelectrolytes in the conscious rat," *Am. J. Physiol.* 253:$H_{299}$–H307, 1978.

26. Ziylan, Y. Z., LeFauconnier, J. M., Bernard, G. et al., "Effect of dexamethasone on transport of alpha-aminoisobutyric acid and sucrose across the blood-brain barrier," *J. Neurochem.* 51:1338–1342, 1988.

What is claimed is:

1. A method for introducing a neuropharmaceutical or neurodiagnostic agent into abnormal brain tissue present in a mammal, said method comprising the steps of:

infusing bradykinin or bradykinin analog into the carotid artery of said mammal, said bradykinin or bradykinin analog being infused into said mammal at a rate of between about 0.05 µg/kg body weight/minute and 20 µg/kg body weight/minute.

2. A method according to claim 1 wherein said bradykinin or bradykinin analog is infused into said carotid artery over a period of between about 5 minutes to about 20 minutes.

3. A method according to claim 1 wherein said neuropharmaceutical agent has a molecular weight of between about 100 and 70,000.

4. A method according to claim 3 wherein said neuropharmaceutical agent is an anti-tumor agent.

5. A method according to claim 1 wherein said neuropharmaceutical agent is administered simultaneously with the infusion of bradykinin or bradykinin analog into said carotid artery.

6. A method according to claim 5 wherein said neuropharmaceutical agent is administered by infusion into said carotid artery.

7. A method according to claim 5 wherein said neuropharmaceutical agent is an anti-tumor agent.

8. A method according to claim 6 wherein said neuropharmaceutical agent is an anti-tumor agent, 9. A method according to claim 1 wherein said bradykinin analog is RMP-7.

10. A method for selectively opening abnormal brain tissue capillaries of a mammal, said method comprising the step of infusing bradykinin or a bradykinin analog into the carotid artery of said mammal, said bradykinin or bradykinin analog being infused into said mammal at a rate of between 0.05 µg/kg body weight/minute and 20 µg/kg body weight/minute.

11. A method according to claim 10 wherein said bradykinin or bradykinin analog is infused into said carotid artery over a period of between about 5 minutes to about 20 minutes.

12. A method for selectively opening abnormal brain tissue capillaries of a mammal according to claim 10 wherein the bradykinin analog RMP-7 is administered to the carotid artery of said mammal.

* * * * *